United States Patent
Mostrorocco

[11] Patent Number: 5,446,596
[45] Date of Patent: Aug. 29, 1995

[54] OPHTHALMIC LENS HOLDER

[76] Inventor: Stephen Mostrorocco, 16 Argyle Pl., Smithtown, N.Y. 11787

[21] Appl. No.: 84,175

[22] Filed: Jul. 1, 1993

[51] Int. Cl.$^6$ .............. G02B 7/02; A61B 3/04
[52] U.S. Cl. .................. 359/827; 359/815; 359/819; 351/41; 351/227
[58] Field of Search ............... 359/800–813, 359/823, 825–827, 896, 817; 351/41–52, 155, 158, 227–235; 33/507; 269/156, 239, 254 R; 451/365, 384, 390

[56] References Cited

U.S. PATENT DOCUMENTS

| | | | |
|---|---|---|---|
| 803,794 | 11/1905 | Starbuck | 33/507 |
| 839,599 | 12/1906 | Kemler | 359/817 |
| 1,142,956 | 6/1915 | Greenberg et al. | 269/254 R |
| 1,258,417 | 3/1918 | Kellner | 351/230 |
| 1,375,669 | 4/1921 | Boutelle | 351/229 |
| 2,533,747 | 12/1950 | Thienemann | 359/804 |
| 3,076,645 | 2/1963 | Neuwirth | 269/254 R |
| 4,381,143 | 4/1983 | Bommarito | 351/227 |
| 4,468,874 | 9/1984 | Chiodo | 359/817 |
| 4,669,226 | 6/1987 | Mandler | 269/22 |
| 4,703,964 | 11/1987 | Ranani | 359/812 |
| 4,915,986 | 4/1990 | Elias et al. | 427/164 |
| 4,997,267 | 3/1991 | Morrison et al. | 351/41 |

FOREIGN PATENT DOCUMENTS 39664  11/1981  European Pat. Off. ............ 351/178

Primary Examiner—Loha Ben
Assistant Examiner—Thong Nguyen
Attorney, Agent, or Firm—Jacobson, Price, Holman & Stern

[57] ABSTRACT

An ophthalmic lens holder for holding lenses in a tinting bath has an upright support with oppositely directed base channels and spring loaded pivoted clamping arms over the base channels. Lenses are held side by side between the clamping arms and the base channels. The holder is designed to facilitate insertion and viewing of the lenses.

10 Claims, 2 Drawing Sheets

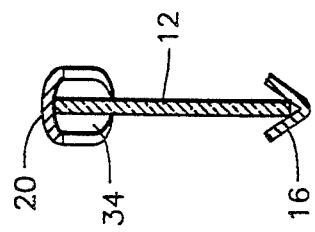
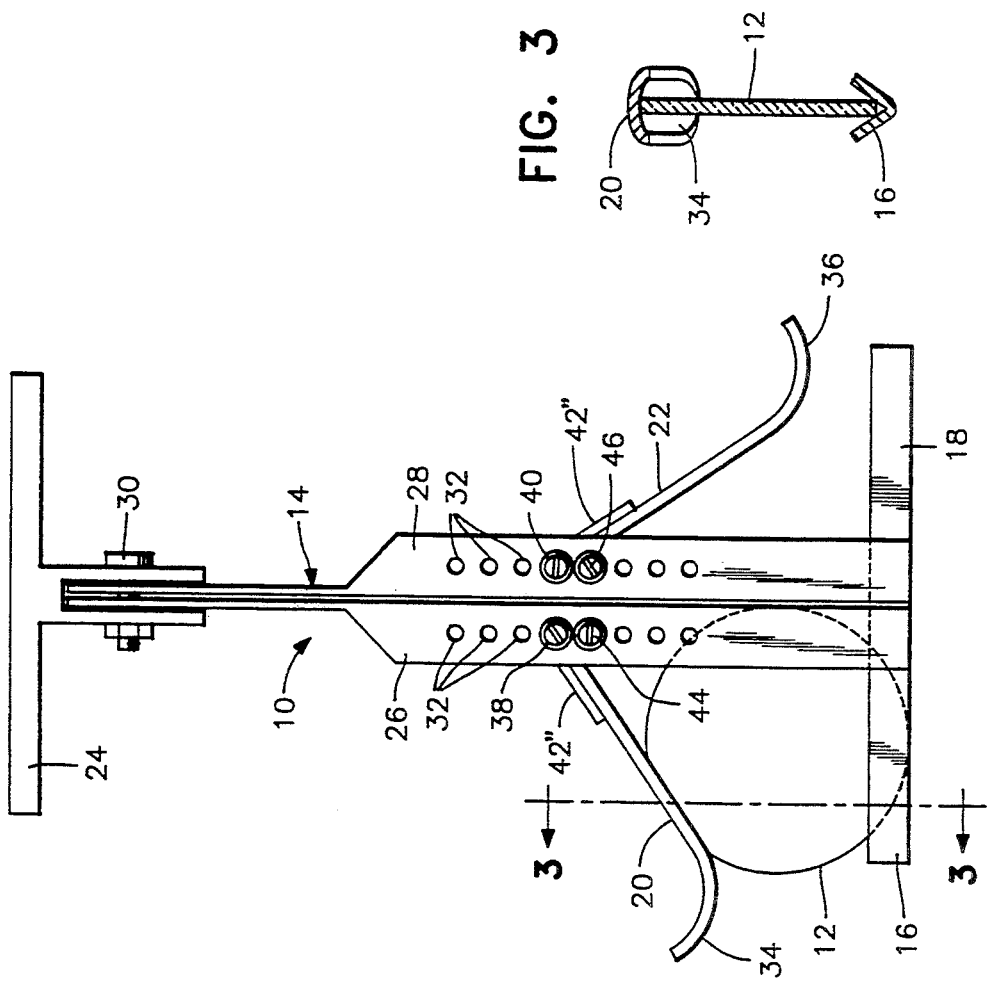
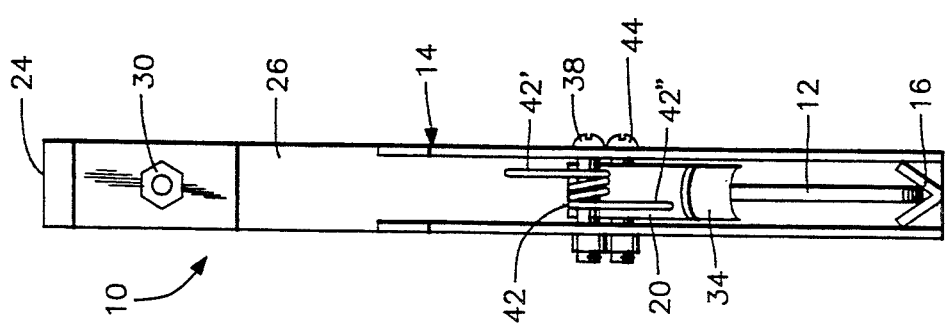

OPHTHALMIC LENS HOLDER

BACKGROUND OF THE INVENTION

This invention relates to an ophthalmic lens holder of the type used, for example, for holding pairs of lenses in a tinting bath.

Known lens holders for the above purpose typically comprise a pair of metal rods, vertically oriented, with a plastic base and a sliding plastic clamp. The clamp can be adjusted vertically along the rods to clamp a pair of lenses back to back between the clamp and the base.

The known lens holders may be said to have certain drawbacks. For example, at least in the simpler designs, the holders can only hold two lenses of the same shape and size simultaneously. Also, during tinting, it is commonly necessary to remove the lenses frequently from the tinting bath to inspect for depth and uniformity of tinting, and to compare the tint of respective lenses. With the known holders, where the lenses are clamped back to back one behind another, it is necessary to remove the lenses for comparing their tint. Also, with the known holders, insertion and removal of lenses is a two-hand operation, one hand gripping the lens and the other hand manipulating the clamp. Further, the sliding clamps may tend to jam.

SUMMARY OF THE INVENTION

It is an object of the invention to provide an improved and entirely novel form of ophthalmic lens holder for the purpose described.

More particularly, it is an object of the invention to provide a lens holder which is conceptually and structurally different from the known holders insofar as it holds a pair of lenses, which may be of the same or different size and shape, in side by side relation rather than back to back so that, inter alia, it may be possible to inspect and compare the tint of the lenses without having to remove them from the holder.

Another object of the invention is to provide a lens holder as aforesaid in which individual lenses can be inserted using only one hand without having to manipulate a clamping mechanism.

In fulfillment of the above and other objects, the invention accordingly provides an ophthalmic lens holder comprising an upright support with a pair of fixed oppositely directed substantially V-shaped channels extending therefrom, a pair of oppositely directed pivotal clamping arms with a concave cross-section, extending from the support above the respective channels and respective spring means urging the respective arms downwardly towards the channels whereby an ophthalmic lens can be inserted in upright position between a respective arm and channel to be clamped peripherally therebetween by downward pressure of the arm produced by the respective spring means.

Preferably, the free end of each arm is curved upwardly to provide a lead-in ramp surface facilitating one-handed insertion of lens. While the pivotal nature of the arms in itself allows lenses of somewhat different size to be accommodated, nevertheless the arms may have releasable attachment means connecting same to the upright, so that the vertical position of the arms can be adjusted along the upright, preferably independently, to accommodate greater variations in lens size.

Holders according to the invention can be constructed with a single set or plural superposed sets of channels and clamping arms to accommodate a single pair or multiple pairs of lenses.

With a pair of lenses positioned side by side in the holder, rather than back to back, in order to compare the tint of the lenses upon removal of the holder from a tinting bath, the holder with the lenses in place can, for example, be held against a suitably uniform light background without having to remove the lenses from the holder as previously. Another advantage of the invention is the ease with which lenses can be inserted and removed due to the design of the spring arms. Additional features and advantages of the invention will become apparent from the ensuing description and claims read in conjunction with the attached drawings.

BRIEF DESCRIPTION OF THE DRAWINGS

FIG. 1 is a front elevational view of a holder for a pair of ophthalmic lenses;

FIG. 2 is an end elevational view of the holder;

FIG. 3 is a sectional view on line 3—3 of FIG. 1; and

DESCRIPTION OF PREFERRED EMBODIMENTS

Figure 4:
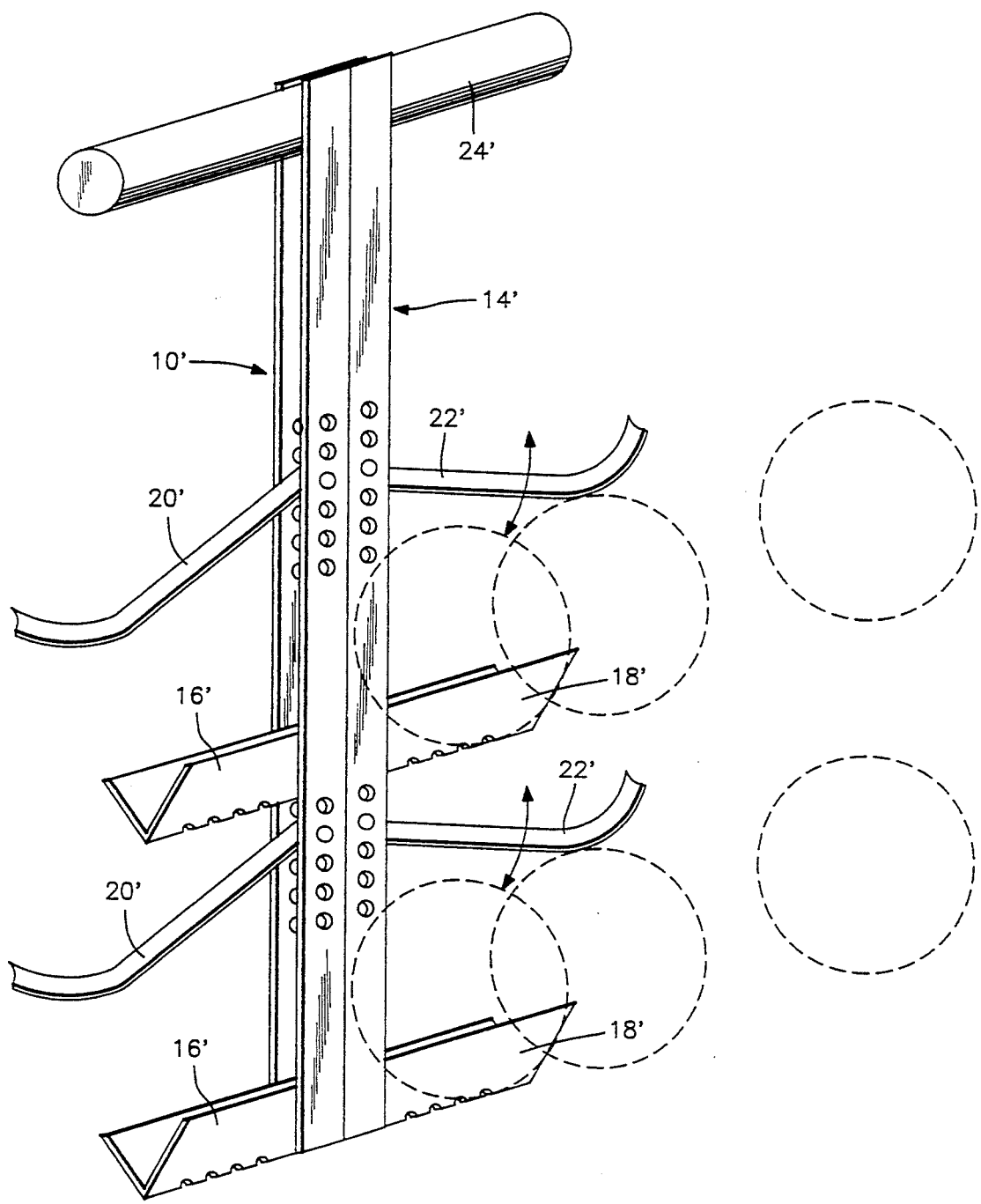
FIG. 4 is a somewhat diagrammatic perspective view of a holder for two pairs of lenses.

Referring initially to FIGS. 1 to 3, a holder 10 for a pair of ophthalmic lenses, only one of which is shown at 12, comprises generally an upright support 14, a pair of base channels 16, 18 extending in opposite directions from the support, a pair of pivoted clamping arms 20, 22 over the respective channels, and a T-bar handle 24 atop the support. All of the components, with the possible exception of the handle which may be plastic, preferably may be made of stainless steel.

Support 14 is conveniently constructed from a pair of channel-shaped uprights 26, 28 welded together back to back with the side walls cut away at the top to receive handle 24 which may be attached by a screw and nut connection 30. The base channels 16, 18 have a substantially V-shaped cross-section and are welded to the bottom of the respective uprights 26, 28. The side walls of the uprights have rows of apertures 32 for adjustably mounting the clamping arms 20, 22 as will be described.

The clamping arms each have a concave cross-section, as best seen in FIG. 3 and are curved upwardly at the outer ends to provide lead-in ramp surfaces 34, 36. At their inner ends, the arms are shaped as journals for receipt on respective mounting pins 38, 40 secured in a selected pair of the apertures 32. The journals have central cut-outs to accommodate coil springs 42 on the pins 38, 40. The coil springs have upper arms 42' engaging one of the uprights 26, 28 and lower arms 42" engaging one of the clamping arms, whereby the arms are spring-urged downwardly towards the respective base channels. Further, de-mountable pins 44, 46 form stops for the clamping arms.

With the above arrangement, lenses can be readily inserted into the holder from each side simply by pushing the lens against the respective ramp surface 34 or 36. This causes the respective clamping arm to lift against the spring pressure so that the lens becomes clamped peripherly between the arm and respective base channel. This operation can be performed with one hand. For larger or smaller size lenses, the clamping arms can be moved to different apertures 32 and thus, the holder can be used for different size lenses on the two sides. The holder is simple to manipulate and lenses can be easily inserted and removed. In use, the lenses are securely clamped between the clamping arms, the uprights and the base channels.

FIG. 4 diagrammatically illustrates a holder 10' which is in all respects similar in construction to holder 10 except that it has superposed sets of clamping arms 20', 22' and base channels 16', 18' to accommodate two pairs of lenses side by side. The holder again has an upright support 14' and a handle 24'.

While only preferred embodiments of the invention have been described herein in detail, the invention is not limited thereby and modifications are possible within the scope of the attached claims.

I claim:

1. A lens holder comprising an upright support, a base channel extending transversely from one side of the support, a handle atop the support, a clamping arm, attachment means pivotally securing an inner end of the clamping arm to the support about an axis perpendicular to the support so that the clamping arm extends over the base channel, and a spring means for urging the clamping arm towards the base channel whereby an ophthalmic lens inserted between the clamping arm and base channel can be clamped peripherally therebetween by pressure from the spring means, wherein the base channel, the clamping arm, the attachment means and the spring means are replicated on an opposite side of the support whereby the holder is adapted to hold a pair of ophthalmic lenses side by side.

2. A lens holder as claimed in claim 1, wherein the base channels, the clamping arms, the attachment means and the spring means are replicated in superposed pairs on opposite sides of the support whereby the holder is adapted to hold superposed pairs of lenses side by side.

3. A lens holder comprising an upright support, a base channel extending transversely from one side of the support, a handle atop the support, a clamping arm, attachment means pivotally securing an inner end of the clamping arm to the support about an axis perpendicular to the support so that the clamping arm extends over the base channel, and a spring means for urging the clamping arm towards the base channel whereby an ophthalmic lens inserted between the clamping arm and base channel can be clamped peripherally therebetween by pressure from the spring means, wherein the base channel and clamping arm each have a concave cross-section.

4. A lens holder comprising an upright support, a base channel extending transversely from one side of the support, a handle atop the support, a clamping arm, attachment means pivotally securing an inner end of the clamping arm to the support about an axis perpendicular to the support so that the clamping arm extends over the base channel, and a spring means for urging the clamping arm towards the base channel whereby an ophthalmic lens inserted between the clamping arm and base channel can be clamped peripherally therebetween by pressure from the spring means, wherein the clamping arm has an outer end curving away from the base channel and defining a lead-in ramp surface facilitating peripheral insertion of a lens between the clamping arm and the base channel.

5. A lens holder comprising an upright support, a base channel extending transversely from one side of the support, a handle atop the support, a clamping arm, attachment means pivotally securing an inner end of the clamping arm to the support about an axis perpendicular to the support so that the clamping arm extends over the base channel, and a spring means for urging the clamping arm towards the base channel whereby an ophthalmic lens inserted between the clamping arm and base channel can be clamped peripherally therebetween by pressure from the spring means, further including stop means on the support for limiting downward pivotal movement of the clamping arm.

6. A lens holder comprising an upright support, a base channel extending transversely from one side of the support, a handle atop the support, a clamping arm, attachment means pivotally securing an inner end of the clamping arm to the support about an axis perpendicular to the support so that the clamping arm extends over the base channel, and a spring means for urging the clamping arm towards the base channel whereby an ophthalmic lens inserted between the clamping arm and base channel can be clamped peripherally therebetween by pressure from the spring means, further including adjustment means for selectively moving the attachment means along the support to provide adjustment of a distance between the clamping arm and the base channel to suit different size lenses.

7. An ophthalmic lens holder comprising an upright support, a handle atop the support, a pair of base channels extending transversely in opposite directions from the support, a pair of clamping arms, attachment means pivotally securing inner ends of the respective clamping arms to the support so that the clamping arms extend over the respective base channels, and spring means for urging the clamping arms towards the respective base channels whereby a pair of ophthalmic lenses can be peripherally clamped between the respective arms and base channels in side by side relation.

8. A lens holder as claimed in claim 7, wherein the base channels and clamping arms each have a concave cross-section and wherein the clamping arms have outer ends curved upwardly away from the base channels to define lead-in ramp surfaces facilitating insertion of the lenses.

9. A lens holder as claimed in claim 7, further including adjustment means for selectively moving a position of the attachment means along the support to vary a distance between the clamping arms and the base channels.

10. A lens holder as claimed in claim 7, wherein the base channels, clamping arms, attachment means and spring means are replicated in superimposed relation on the support to receive another pair of lenses side by side.

* * * * *